United States Patent
Cheng et al.

(10) Patent No.: US 11,081,348 B2
(45) Date of Patent: Aug. 3, 2021

(54) SELECTIVE DEPOSITION OF SILICON USING DEPOSITION-TREAT-ETCH PROCESS

(71) Applicant: Applied Materials, Inc., Santa Clara, CA (US)

(72) Inventors: Rui Cheng, Santa Clara, CA (US); Fei Wang, Fremont, CA (US); Abhijit Basu Mallick, Palo Alto, CA (US); Robert Jan Visser, Menlo Park, CA (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 0 days.

(21) Appl. No.: 16/001,251

(22) Filed: Jun. 6, 2018

(65) Prior Publication Data

US 2018/0350597 A1    Dec. 6, 2018
US 2020/0144060 A9    May 7, 2020

Related U.S. Application Data

(60) Provisional application No. 62/515,852, filed on Jun. 6, 2017.

(51) Int. Cl.
*H01L 21/02* (2006.01)
*A61K 9/00* (2006.01)
(Continued)

(52) U.S. Cl.
CPC ...... *H01L 21/02636* (2013.01); *A61K 9/0024* (2013.01); *A61K 31/438* (2013.01); *A61K 31/4409* (2013.01); *A61K 31/47* (2013.01); *A61K 31/497* (2013.01); *A61K 47/12* (2013.01); *A61K 47/26* (2013.01); *A61K 47/36* (2013.01); *H01L 21/0262* (2013.01); *H01L 21/02381* (2013.01); *H01L 21/02488* (2013.01);
(Continued)

(58) Field of Classification Search
CPC .......... H01L 21/02636–02653; H01L 21/2018
See application file for complete search history.

(56) References Cited

U.S. PATENT DOCUMENTS

| | | | | |
|---|---|---|---|---|
| 5,242,530 A | * | 9/1993 | Batey | C23C 16/04 |
| | | | | 117/90 |
| 2003/0045075 A1 | * | 3/2003 | Joo | C30B 25/02 |
| | | | | 438/507 |

(Continued)

FOREIGN PATENT DOCUMENTS

JP    2015065393 A    4/2015

OTHER PUBLICATIONS

PCT International Search Report and Written Opinion in PCT/US2018/036241 dated Sep. 21, 2018, 11 pages.
Mahajan, A., et al., "Si Atomic Layer Epitaxy Based on Si2H6 and Remote He Plasma Bombardment", Office of Naval Research, Contract N00014-91-J-1513, 19 pages.

*Primary Examiner* — Bryan R Junge
(74) *Attorney, Agent, or Firm* — Servilla Whitney LLC

(57) ABSTRACT

Methods for selective silicon film deposition on a substrate comprising a first surface and a second surface are described. More specifically, the process of depositing a film, treating the film to change some film property and selectively etching the film from various surfaces of the substrate are described. The deposition, treatment and etching can be repeated to selectively deposit a film on one of the two substrate surfaces.

20 Claims, 1 Drawing Sheet

(51) Int. Cl.
*A61K 31/438* (2006.01)
*A61K 31/4409* (2006.01)
*A61K 31/47* (2006.01)
*A61K 31/497* (2006.01)
*A61K 47/12* (2006.01)
*A61K 47/26* (2006.01)
*A61K 47/36* (2006.01)
*H01L 21/3065* (2006.01)

(52) U.S. Cl.
CPC .. *H01L 21/02491* (2013.01); *H01L 21/02532* (2013.01); *H01L 21/02639* (2013.01); *H01L 21/02642* (2013.01); *H01L 21/02664* (2013.01); *H01L 21/3065* (2013.01)

(56) References Cited

U.S. PATENT DOCUMENTS

| | | |
|---|---|---|
| 2006/0115933 A1* | 6/2006 | Ye .................... H01L 21/02381 438/139 |
| 2006/0286764 A1 | 12/2006 | Zhang et al. |
| 2008/0026149 A1 | 1/2008 | Tomasini et al. |
| 2010/0144129 A1* | 6/2010 | Lee ...................... C30B 25/105 438/488 |
| 2012/0210932 A1* | 8/2012 | Hekmatshoar-Tabari ................... C30B 25/105 117/103 |
| 2015/0162214 A1 | 6/2015 | Thompson et al. |
| 2015/0221542 A1 | 8/2015 | Knisley et al. |
| 2016/0141179 A1 | 5/2016 | Wu et al. |
| 2016/0293398 A1 | 10/2016 | Danek et al. |

\* cited by examiner

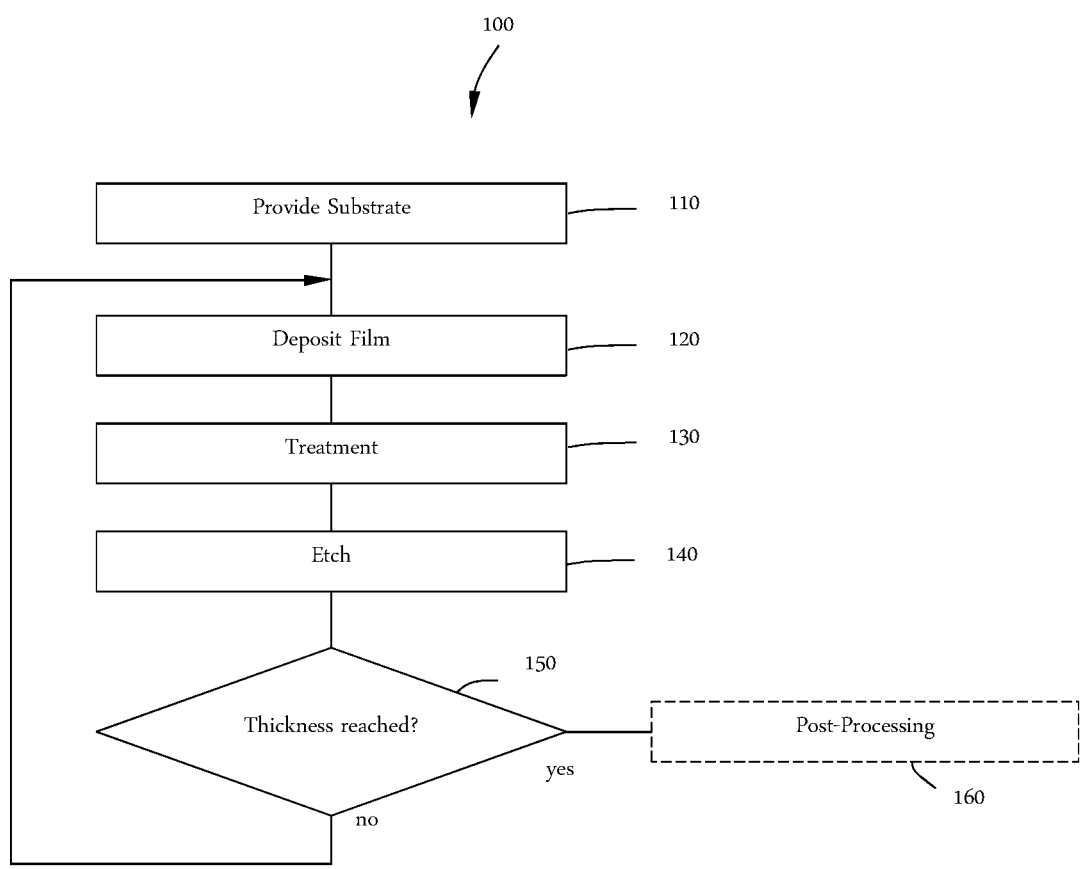

SELECTIVE DEPOSITION OF SILICON USING DEPOSITION-TREAT-ETCH PROCESS

CROSS-REFERENCE TO RELATED APPLICATIONS

This application claims priority to U.S. Provisional Application No. 62/515,852, filed Jun. 6, 2017, the entire disclosure of which is hereby incorporated by reference herein.

TECHNICAL FIELD

The present disclosure relates generally to methods of selectively depositing silicon films. In particular, the disclosure relates to processes for selectively depositing a silicon layer with a multi-stage deposition-treat-etch process.

BACKGROUND

Forming films on a substrate by chemical reaction of gases is one of the primary steps in the fabrication of modern semiconductor devices. These deposition processes include chemical vapor deposition (CVD) as well as plasma enhanced chemical vapor deposition (PECVD), which uses plasma in combination with traditional CVD techniques.

Selective deposition processes are becoming more frequently employed because of the need for patterning applications for semiconductors. Traditionally, patterning in the microelectronics industry has been accomplished using various lithography and etch processes. However, since lithography is becoming exponentially complex and expensive the use of selective deposition to deposit features is becoming much more attractive.

As device sizes continue to decrease to less than the 10 nm regime, traditional patterning processes using photolithography technology is becoming more challenging. Non-precise patterning and degraded device performance are more prevalent at lower device sizes. Additionally, the multiple patterning technologies also make fabrication processes complicated and more expensive.

Therefore, there is a need in the art for methods to selectively deposit a film onto one surface over a different surface.

SUMMARY

One or more embodiments of the disclosure are directed to a method of selectively depositing a film wherein a substrate is provided having a first surface and a second surface. The substrate is exposed to a silane and a deposition plasma to deposit a silicon film on the first surface and the second surface, the silicon film having different properties on the first surface and on the second surface. The silicon film is exposed to a treatment plasma to modify a structure, composition or morphology of the silicon film on one or more of the first surface or the second surface, the treatment plasma comprising plasmas of one or more of Ar, He, or $H_2$. The film is etched from the first surface and the second surface to remove substantially all of the film from the second surface and leave at least some of the silicon film on the first surface. The deposition, treatment and etching are repeated to form a film selectively on the first surface over the second surface.

Additional embodiments of the disclosure are directed to a method of selectively depositing a film wherein a substrate is provided having a first surface consisting essentially of silicon and a second surface comprised of at least one different material. The substrate is exposed to $SiH_4$ and a hydrogen plasma to deposit a silicon film on the first surface and the second surface, the silicon film having different properties on the first surface and on the second surface. The silicon film is exposed to a treatment plasma to modify a structure, composition or morphology of the silicon film on one or more of the first surface or the second surface, the treatment plasma comprising plasmas of one or more of Ar, He, or $H_2$. The film is etched from the first surface and the second surface with a thermal etch to remove substantially all of the film from the second surface and leave at least some of the silicon film on the first surface. The deposition, treatment and etching are repeated to form a film selectively on the first surface over the second surface.

Further embodiments of the disclosure are directed to a method of selectively depositing a film wherein a substrate is provided having a first surface consisting essentially of silicon and a second surface comprised of at least one different material. The substrate is exposed to $SiH_4$ and a hydrogen plasma to deposit a silicon film on the first surface and the second surface, the silicon film having different properties on the first surface and on the second surface. The silicon film is exposed to a treatment plasma to modify a structure, composition or morphology of the silicon film on one or more of the first surface or the second surface, the treatment plasma comprising plasmas of one or more of Ar, He, or $H_2$. The film is etched from the first surface and the second surface with a plasma etch to remove substantially all of the film from the second surface and leave at least some of the silicon film on the first surface. The deposition, treatment and etching are repeated to form a film selectively on the first surface over the second surface.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

The FIGURE shows a process flow in accordance with one or more embodiments of the disclosure.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

A "substrate" as used herein, refers to any substrate or material surface formed on a substrate upon which film processing is performed during a fabrication process. For example, a substrate surface on which processing can be performed include materials such as silicon, silicon oxide, strained silicon, silicon on insulator (SOI), carbon doped silicon oxides, amorphous silicon, doped silicon, germanium, gallium arsenide, glass, sapphire, and any other materials such as metals, metal nitrides, metal alloys, and other conductive materials, depending on the application. Substrates include, without limitation, semiconductor wafers.

Substrates may be exposed to a pretreatment process to polish, etch, reduce, oxidize, hydroxylate, anneal, UV cure, e-beam cure and/or bake the substrate surface. In addition to film processing directly on the surface of the substrate itself, in the present invention, any of the film processing steps disclosed may also be performed on an underlayer formed on the substrate as disclosed in more detail below, and the term "substrate surface" is intended to include such underlayer as the context indicates. Thus for example, where a film/layer or partial film/layer has been deposited onto a substrate surface, the exposed surface of the newly deposited film/layer becomes the substrate surface.

Embodiments of the disclosure provide methods of selectively depositing a film (e.g., silicon) on a substrate with varied surface compositions. Some embodiments advantageously provide methods involving cyclic deposition-treatment-etch processes that can be performed in a cluster tool environment. Some embodiments advantageously deposit silicon films on silicon surfaces over other surfaces.

Without being bound by any particular theory of operation, it is believed that the nucleation of materials (e.g., Si) is different on different surfaces. Therefore, the nucleation on a film with different degrees of crystallinity will be different. Additionally, the etch rate of materials (e.g., Si) will be different on different surfaces. Some embodiments advantageously provide methods that use plasma to etch materials (e.g., Si) faster on certain surfaces than on other surfaces. Some embodiments advantageously use the different etch rates on different surfaces to create selective deposition of a silicon film by cycling the deposition-treatment-etch process.

The FIGURE shows an exemplary processing method 100 in accordance with one or more embodiments of the disclosure. A substrate having a first surface and a second surface is provided for processing at 110. As used in this regard, the term "provided" means that the substrate is placed into a position or environment for further processing. The first surface and the second surface are different materials. For example, one of the surfaces may be silicon and the other a metal. In some embodiments, the first surface and the second surface have the same chemical composition but different physical properties (e.g., crystallinity).

The first surface can be any suitable material including, but not limited to, metallic films. In some embodiments, the first surface is metallic comprising one or more of silicon, tungsten, cobalt, copper, ruthenium, palladium, platinum, nickel, chromium, manganese, iron, zirconium, molybdenum, niobium, silver, hafnium, tantalum, or a lanthanide. In some embodiments, the first surface consists essentially of silicon. As used in this manner, the term "consists essentially of" means that the surface is greater than or equal to about 95%, 98% or 99% silicon on an atomic basis.

The second surface can be any suitable surface that is different from the first surface. The difference between the first surface and the second surface can be based on film composition or on some physical property of the film. In some embodiments, the second surface comprises a metal boride, metal oxide, metal nitride, metal carbide, metal oxycarbide, metal oxynitride, metal oxyboride, metal boronitride, metal borocarbide, metal carbonitride, metal oxycarbonitride, metal borocarbonitride, metal borooxynitride, metal oxyborocarbonitride, or combinations thereof. In some embodiments, the second surface comprises a dielectric material having either a low dielectric constant (k<5) or a high dielectric constant (k>=5). In some embodiments, the second surface comprises one or more of silicon oxide, silicon nitride.

In some embodiments, the first surface comprises a metal surface and the second surface comprises a similar metal as the first surface with different crystallinity than the first surface. In some embodiments, the first surface and the second surface comprise dielectric materials with different crystal structures, densities and/or surface terminations.

While the description of the process in the FIGURE is presented with respect to a substrate with a first surface comprising silicon and a second surface comprising one or more of silicon oxide or silicon nitride, those skilled in the art will recognize that this is merely representative of one possible configuration and that other combinations are within the scope of the disclosure. The substrate is exposed at 120 to a silane and a deposition plasma. For the purposes of this disclosure, this exposure is referred to as the deposition. In some embodiments, the silane comprises at least one species with the formula $Si_nH_{2n+2}$. In some embodiments, the silane consists essentially of $SiH_4$. In some embodiments, the silane consists essentially of $Si_2H_6$. In some embodiments, the silane consists essentially of dichlorosilane, $SiH_2Cl_2$. As used in this manner, the term "consists essentially of" means that the silane is greater than or equal to about 95%, 98% or 99% of the stated species on a weight basis. In some embodiments, the silane comprises a silicon halide species where the halogen atoms comprise one or more of Cl, Br and I. In some embodiments, the silicon halide comprises substantially no fluorine atoms. As used in this manner, the term "substantially no fluorine atoms" means that the composition of the halogen species is less than or equal to about 95%, 98% or 99% fluorine, on an atomic basis.

In some embodiments, the deposition plasma comprises one or more of Ar, He, $H_2$ or $N_2$. In some embodiments, the deposition plasma consists essentially of Ar. In some embodiments, the deposition plasma consists essentially of He. In some embodiments, the deposition plasma consists essentially of $H_2$. In some embodiments, the deposition plasma consists essentially of $N_2$. As used in this manner, the term "consists essentially of" means that the deposition plasma is greater than or equal to about 95%, 98% or 99% of the stated species on an atomic basis.

The deposition plasma can be a conductively-coupled plasma (CCP) or inductively coupled plasma (ICP) and can be a direct plasma or a remote plasma. In some embodiments, the deposition plasma has a power in the range of about 0 W to about 2000 W. In some embodiments, the minimum plasma power is greater than 0 W, 10 W, 50 W or 100 W.

The temperature during deposition 120 can be any suitable temperature depending on, for example, the precursor(s) and/or deposition plasma(s) being used. In some embodiments, the deposition temperature is in the range of about 100° C. to 500° C., or in the range of about 150° C. to about 450° C., or in the range of about 200° C. to about 400° C.

The processing chamber pressure during deposition 120 can be in the range of about 100 mTorr to 300 Torr, or in the range of about 200 mTorr to about 250 Torr, or in the range of about 500 mTorr to about 200 Torr, or in the range of about 1 Torr to about 150 Torr.

As identified previously, the nucleation of the silicon film on the first surface and the second surface may impact the thickness as well as the physical properties of the film deposited as a result of the silane/plasma exposure at 120 on the first surface and the second surface. In some embodiments, the crystallinity of the silicon film deposited on the first surface and the second surface is different after deposition.

The film deposited can be any suitable thickness before moving to the treatment process. In some embodiments, the thickness of the deposited film is greater than or equal to about 5 Å, 10 Å, 15 Å, 20 Å or 25 Å before moving to the treatment process. In some embodiments, the thickness of the deposited film is less than or equal to about 100 Å, 90 Å, 80 Å, 70 Å, 60 Å or 50 Å before moving to the treatment process.

After deposition, the substrate is exposed to a treatment plasma at 130 to modify a structure, composition or morphology of the silicon film on the first surface and/or the second surface. For the purposes of this disclosure, this exposure is referred to as the treatment.

In some embodiments, the treatment plasma comprises one or more of Ar, He, or $H_2$. In some embodiments, the treatment plasma consists essentially of Ar. In some embodiments, the treatment plasma consists essentially of He. In some embodiments, the treatment plasma consists essentially of $H_2$. As used in this manner, the term "consists essentially of" means that the treatment plasma is greater than or equal to about 95%, 98% or 99% of the stated species on an atomic basis. In some embodiments, the treatment plasma is the same as the deposition plasma. In some embodiments, the treatment plasma is different than the deposition plasma.

The treatment plasma can be a conductively-coupled plasma (CCP) or inductively coupled plasma (ICP) and can be a direct plasma or a remote plasma. In some embodiments, the plasma has a power in the range of about 0 to about 2000 W. In some embodiments, the minimum plasma power is greater than 0 W, 10 W, 50 W or 100 W.

The temperature during treatment 130 can be any suitable temperature depending on, for example, the treatment plasma(s) being used. In some embodiments, the treatment temperature is in the range of about 100° C. to 500° C., or in the range of about 150° C. to about 450° C., or in the range of about 200° C. to about 400° C.

The processing chamber pressure during treatment 130 can be in the range of about 100 mTorr to 300 Torr, or in the range of about 200 mTorr to about 250 Torr, or in the range of about 500 mTorr to about 200 Torr, or in the range of about 1 Torr to about 150 Torr.

As identified previously, the structure, composition or morphology of the silicon film on the first surface and the second surface will be different as a result of the treatment plasma exposure at 130. In some embodiments, the crystallinity of the silicon film on the first surface and the second surface is different after treatment. In some embodiments, the crystallinity of the silicon film on the first surface and the second surface is different before treatment and after treatment the difference between the crystallinities is greater than before treatment.

After treatment, the substrate is etched at 140 to remove substantially all of the silicon film from the second surface and leave at least some of the silicon film on the first surface. As used in this manner, the term "substantially all" means that enough of the film from the second surface has been removed to provide a nucleation delay for a subsequent deposition process. In some embodiments, removing substantially all of the film from the second surface means that at least about 95%, 98% or 99% of the film from the second surface has been etched or removed.

In some embodiments, the film is etched with a thermal etch process. For the purposes of this disclosure a thermal etch process may utilize an etchant as a reactant in a thermal etch process. In some embodiments, the thermal etch process is performed with an etchant comprising $H_2$. In some embodiments, an inert gas is co-flowed with the etchant during the thermal etch process.

In some embodiments, the film is etched with a plasma etch process. For the purposes of this disclosure, the plasma utilized in the plasma etch process is referred to as the etching plasma. In some embodiments, the etching plasma comprises one or more of $H_2$, HCl, $Cl_2$, or $NF_3$. In some embodiments, the etching plasma consists essentially of $H_2$. In some embodiments, the etching plasma consists essentially of HCl. In some embodiments, the etching plasma consists essentially of $Cl_2$. In some embodiments, the etching plasma consists essentially of $NF_3$. As used in this manner, the term "consists essentially of" means that the etching plasma is greater than or equal to about 95%, 98% or 99% of the stated species on an atomic basis. In some embodiments, an inert gas is co-flowed with the etching plasma during the plasma etch process.

The etching plasma can be a conductively-coupled plasma (CCP) or inductively coupled plasma (ICP) and can be a direct plasma or a remote plasma. In some embodiments, the plasma has a power in the range of about 0 to about 2000 W. In some embodiments, the minimum plasma power is greater than 0 W, 10 W, 50 W or 100 W.

The temperature during etch 130 can be any suitable temperature depending on, for example, the etch process, the etchant and/or the etching plasma(s) being used. In some embodiments, the etch temperature is in the range of about 100° C. to 500° C., or in the range of about 150° C. to about 450° C., or in the range of about 200° C. to about 400° C.

The processing chamber pressure during etch 140 can be in the range of about 100 mTorr to 300 Torr, or in the range of about 200 mTorr to about 250 Torr, or in the range of about 500 mTorr to about 200 Torr, or in the range of about 1 Torr to about 150 Torr.

After etching the method 100 reaches decision point 150. If the silicon film has reached a predetermined thickness on the first layer, the substrate optionally continues for further post-processing at 160. If the silicon film has not reached a predetermined thickness on the first layer, the method returns to 120 for at least one additional cycle of "deposit"-"treatment"-"etch".

Some embodiments include an optional post-processing 160 process. The post-processing 160 can be used to modify the deposited film or the substrate to improve some parameter of the film or substrate. In some embodiments, the post-processing 160 comprises annealing the film. In some embodiments, post-processing 160 can be performed by in-situ anneal in the same process chamber used for deposition 120, treatment 130 and/or etch 140. Suitable annealing processes include, but are not limited to, rapid thermal processing (RTP) or rapid thermal anneal (RTA), spike anneal, or UV cure, or e-beam cure and/or laser anneal. The anneal temperature can be in the range of about 500° C. to 900° C. The composition of the environment during anneal may include one or more of $H_2$, Ar, He, $N_2$, $NH_3$, $SiH_4$, etc. The pressure during the anneal can be in the range of about 100 mTorr to about 1 atm.

At any point during the methods described by this disclosure, the substrate can be heated or cooled. Such heating or cooling can be accomplished by any suitable means including, but not limited to, changing the temperature of the substrate support and flowing heated or cooled gases to the substrate surface. In some embodiments, the substrate support includes a heater/cooler which can be controlled to change the substrate temperature conductively. In one or more embodiments, the gases (either reactive gases or inert gases) being employed are heated or cooled to locally change the substrate temperature. In some embodiments, a heater/cooler is positioned within the chamber adjacent the substrate surface to convectively change the substrate temperature.

The substrate can also be stationary or rotated during processing. A rotating substrate can be rotated continuously or in discreet steps. For example, a substrate may be rotated throughout the entire process, or the substrate can be rotated by a small amount between exposures to different reactive gases, purge gases, reactants or plasmas. Rotating the substrate during processing (either continuously or in steps) may help produce a more uniform deposition, treatment or etch by minimizing the effect of, for example, local variability in gas flow geometries.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in some embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method of selectively depositing a film, the method comprising:
    exposing a substrate having a first surface and a second surface to a silane and a deposition plasma to deposit a silicon film on the first surface and the second surface, the silicon film on the first surface having a difference in crystallinity from the silicon film on the second surface;
    exposing the silicon film to a treatment plasma to increase the difference in crystallinity between the silicon film on the first surface and the second surface, the treatment plasma comprising plasmas of one or more of Ar, He, or $H_2$;
    etching the film from the first surface and the second surface to remove substantially all of the film from the second surface and leave at least some of the silicon film on the first surface; and
    repeating the deposition, treatment and etching to form a film selectively on the first surface over the second surface.

2. The method of claim 1, wherein the first surface of the substrate consists essentially of silicon.

3. The method of claim 1, wherein the second surface of the substrate comprises one or more of silicon oxide, silicon nitride, glass or a metal.

4. The method of claim 1, wherein the silane comprises at least one species with the general formula $Si_nH_{2n+2}$.

5. The method of claim 3, wherein the silane consists essentially of $SiH_4$.

6. The method of claim 3, wherein the silane consists essentially of $Si_2H_6$.

7. The method of claim 1, wherein the silane consists essentially of $SiH_2Cl_2$ (dichlorosilane or DCS).

8. The method of claim 1, wherein the deposition plasma comprises of one or more of Ar, He, $H_2$ or $N_2$.

9. The method of claim 1, wherein after deposition the crystallinity of the silicon film differs on the first surface and the second surface.

10. The method of claim 1, wherein the treatment plasma consists essentially of a capacitvely coupled plasma.

11. The method of claim 1, wherein the treatment plasma consists essentially of an inductively coupled plasma.

12. The method of claim 1, wherein after treatment the crystallinity of the deposited silicon film differs on the first surface and the second surface.

13. The method of claim 1, wherein the film is etched using a thermal etch process.

14. The method of claim 1, wherein the film is etched using a plasma etch process.

15. The method of claim 14, wherein the film is etched by a plasma comprised of $H_2$, HCl, $Cl_2$, or $NF_3$.

16. The method of claim 15, wherein the film is etched by a plasma consisting essentially of hydrogen.

17. The method of claim 1, wherein the first surface of the substrate comprises a metal surface.

18. The method of claim 17, wherein the metal surface comprises one or more of tungsten, cobalt, copper, ruthenium, palladium, platinum, nickel, chromium, manganese, iron, zirconium, molybdenum, niobium, silver, hafnium, tantalum, or a lanthanide.

19. A method of selectively depositing a film, the method comprising:
    exposing a substrate having a first surface consisting essentially of silicon and a second surface comprised of at least one different material to $SiH_4$ and a hydrogen plasma to deposit a silicon film on the first surface and the second surface, the silicon film on the first surface having a difference in crystallinity from the silicon film on the second surface;
    exposing the silicon film to a treatment plasma to increase the difference in crystallinity between the silicon film on the first surface and the second surface, the treatment plasma comprising plasmas of one or more of Ar, He, or $H_2$;
    etching the film from the first surface and the second surface with a thermal etch to remove substantially all of the film from the second surface and leave at least some of the silicon film on the first surface; and
    repeating the deposition, treatment and etching to form a film selectively on the first surface over the second surface.

20. A method of selectively depositing a film, the method comprising:
    exposing a substrate having a first surface consisting essentially of silicon and a second surface comprised of at least one different material to $SiH_4$ and a hydrogen plasma to deposit a silicon film on the first surface and the second surface, the silicon film on the first surface having a difference in crystallinity from the silicon film on the second surface;
    exposing the silicon film to a treatment plasma to increase the difference in crystallinity between the silicon film on the first surface and the second surface, the treatment plasma comprising plasmas of one or more of Ar, He, or $H_2$;

etching the film from the first surface and the second surface with a plasma etch to remove substantially all of the film from the second surface and leave at least some of the silicon film on the first surface; and repeating the deposition, treatment and etching to form a film selectively on the first surface over the second surface.

* * * * *